United States Patent [19]

Gustafson

[11] Patent Number: 5,185,476

[45] Date of Patent: * Feb. 9, 1993

[54] LOW PRESSURE CATALYTIC HYDROGENATION OF CARBONYL-CONTAINING COMPOUNDS AND SUPPORTED CATALYSTS THEREFOR

[75] Inventor: Bruce L. Gustafson, Kingsport, Tenn.

[73] Assignee: Eastman Kodak Company, Rochester, N.Y.

[*] Notice: The portion of the term of this patent subsequent to Jun. 6, 2006 has been disclaimed.

[21] Appl. No.: 765,856

[22] Filed: Sep. 26, 1991

Related U.S. Application Data

[63] Continuation of Ser. No. 478,363, Feb. 12, 1990, abandoned, which is a continuation-in-part of Ser. No. 219,630, Jul. 15, 1988, abandoned.

[51] Int. Cl.$^5$ .................. C07C 29/149; C07C 31/08; C07C 31/20; C07C 31/135
[52] U.S. Cl. .................. 568/831; 568/814; 568/864; 568/881; 568/885
[58] Field of Search ............ 568/864, 885, 814, 831, 568/881

[56] References Cited

U.S. PATENT DOCUMENTS 4,837,368  6/1989  Gustafson et al. ............... 568/880

*Primary Examiner*—Joseph E. Evans
*Attorney, Agent, or Firm*—J. Frederick Thomsen; William P. Heath, Jr.

[57] ABSTRACT

Disclosed are novel catalysts useful for the hydrogenation of carbonyl-containing compounds at mild conditions of temperature and pressure to produce alcohols or amines is disclosed. The catalysts comprise palladium and zinc on a catalyst support material and are obtained by the steps of:

(a) providing a catalyst support material on which is deposited zero-valent palladium in a uniformly and highly dispersed form;

(b) contacting the palladium-bearing support material of (a) with zinc or a reducible compound thereof; and, preferably, (c) heating the palladium- and zinc-bearing support of (b) at a temperature of about 200° to 400° C. in the presence of an oxygen-containing gas.

6 Claims, No Drawings

LOW PRESSURE CATALYTIC HYDROGENATION OF CARBONYL-CONTAINING COMPOUNDS AND SUPPORTED CATALYSTS THEREFOR

This is a continuation application of copending application Ser. No. 07/478,383 filed on Feb. 12, 1990, now abandoned, which in turn is a continuation-in-part application of application Ser. No. 07/219,630 filed on Jul. 15, 1988, now abandoned.

This invention relates to catalytic hydrogenation. In one aspect, the present invention relates to a novel catalytic hydrogenation process for the selective reduction of carbonyl-containing compounds to alcohols. In another aspect, the present invention relates to novel supported hydrogenation catalysts useful for the selective reduction of carbonyl-containing compounds to alcohols, and methods for preparing such catalysts.

BACKGROUND OF THE INVENTION

The catalytic hydrogenation of carbonyl-containing compounds, e.g., esters, to produce their corresponding alcohols, is potentially of great commercial value. Catalysts traditionally employed for such conversions include copper chromite based materials, frequently containing a promoter such as barium. Unfortunately, these catalysts typically require high pressure to achieve commercially attractive reaction rates for the hydrogenation of esters, i.e., pressures in excess of 3000 psig. In addition, chromium and barium present toxicity and environmental concerns which must be dealt with if one is to economically and safely use these materials on a commercial scale.

More recently, substantial amounts of research have been carried out in efforts to develop hydrogenation catalysts capable of reducing carbonyl-containing compounds, e.g., organic acids and esters, to alcohols at reduced pressures. While such catalysts are capable of promoting the hydrogenation of carbonyl-containing compounds to produce alcohols, one problem with such materials is the need to run at very low liquid hourly space velocities in order to achieve suitably high conversion levels.

Another problem frequently encountered with such prior art low pressure catalyst systems when employed in the reduction of carbonyl-containing compounds such as aldehydes and ketones, is their lack of selectivity to produce the desired alcohol product, such catalysts frequently being too active and thus producing product which results from reaction of substrate with additional hydrogen.

Yet another problem encountered with such prior art low pressure catalyst systems, such as Raney nickel, is the ease of handling of such catalysts, which are frequently pyrophoric, and thus require special handling to avoid fire hazard.

STATEMENT OF THE INVENTION

In accordance with the present invention, it has been discovered that a supported palladium-zinc catalyst prepared by a specific combination of steps is exceptionally effective for the low pressure hydrogenation of carbonyl-containing compounds to selectively produce alcohols in high yield. These steps include depositing palladium on a support and reducing the palladium sufficiently to "stabilize" the palladium on the support, and then contacting the support bearing highly dispersed, zero-valent palladium with zinc. The novel hydrogenation process provided by this invention employs readily prepared, easily handled catalysts and enables a commercially important reaction, i.e., the conversion of carbonyl-containing compounds to alcohols, to be carried out at low reaction pressures, thereby reducing the cost of equipment required for the desired hydrogenation reaction and reducing the safety risks involved in such conversions.

DETAILED DESCRIPTION OF THE INVENTION

The novel high-activity, low-pressure hydrogenation catalysts provided by the present invention comprises palladium and zinc on a support obtained by the steps comprising:

(a) providing a catalyst support material on which is deposited zero-valent palladium in a uniformly and highly dispersed form; and (b) contacting palladium-bearing support material of (a) with zinc or a compound thereof.

The method by which the novel hydrogenation catalysts are prepared may include an optional calcination step wherein the palladium- and zinc-bearing support material of (b) is heated at a temperature in the range of 200° up to 400° C. in the presence of an oxygen-containing gas to activate the zinc component. In the optional calcination-activation step, the palladium- and zinc bearing catalyst support material is heated for a time sufficient to remove undesired counter-ions and/or ligands.

The palladium-bearing support material of step (a) may be obtained using various procedures known to those skilled in the art. Thus, a wide variety of techniques for contacting support with palladium and zinc are contemplated for use in the practice of the present invention. For example, palladium or a reducible palladium compound can be applied directly to a support material employing such techniques as incipient wetness, wet impregnation, ion exchange, metal atom evaporation or precipitation. After the support material has been contacted with palladium or a reducible palladium compound, and before the support is further treated with zinc, the palladium-treated support is subjected to reducing conditions sufficient to fix the palladium on the support in a highly dispersed and reduced state so that redispersion of the palladium does not occur upon exposure to corrosive zinc species such as nitrates. For example, this can be accomplished by heating the palladium-treated support under a hydrogen atmosphere at a temperature in the range of about 25° up to 400° C.

Suitable sources of palladium are any compounds which are reducible when subjected to reducing conditions. Since many palladium compounds are convertible to the oxide form upon calcination under the above-described conditions, and the oxides of palladium are readily reduced, many palladium compounds are useful for catalyst preparation. Exemplary palladium compounds include the palladium halides, palladium acetate, palladium nitrate, palladium amine complexes, organometallic complexes of palladium, and the like.

A wide range of zinc compounds are suitable sources of zinc for use in the preparation of the novel catalyst composition of the present invention, e.g., zinc nitrate, zinc halides, zinc acetate, zinc carbonate, zinc oxide and the like. Such zinc compounds may be applied to the palladium-bearing catalyst support of Step (a) by conventional methods such as those described hereinabove. When the zinc component of the catalyst initially is provided as a precursor moiety, it is preferred to subject the palladium-bearing, zinc-treated support to a calcination treatment at temperatures in the range of about 200° up to 400° C. Such temperature is maintained for a time sufficient to remove undesired counter-ions and/or ligands, thereby activating the zinc component used to form the catalyst. Times in the range of about 2 up to 8 hours or longer are generally effective for this purpose.

The amount of palladium present on the supported catalyst of the present invention is within the range of about 0.5 up to about 5.0 weight percent, calculated as the metal and based on the total weight of palladium, zinc and support. Typically, the atomic ratio of palladium to zinc falls within the range of about 0.01 up to 2.0, preferably in the range of about 0.2 up to 2.0.

A wide variety of inorganic materials can be employed as the catalyst support material of the novel catalysts of this invention. Exemplary materials include relatively non-acidic that do not promote significant levels of such undesired side reaction as transesterification, alcohol dehydration, ester hydrolysis, and the like. Such materials include silica ($SiO_2$), titania ($TiO_2$), carbon (C), rare earth oxides (e.g., $La_2O_3$, $CeO_2$), alumina ($Al_2O_3$), and the like, as well as mixtures of any two or more thereof. The support preferably is carbon, titania or, especially, silica.

The surface area of the catalyst support material employed in the preparation of the catalysts can vary widely. Preferably, support materials having surface areas of at least about 1 $m^2/g$ will be employed. Of course, those of skill in the art also recognize that higher surface area materials will generally produce higher activity catalysts than lower surface area catalysts having comparable composition.

The novel hydrogenation process provided by the present invention comprises contacting one or more carbonyl compounds such as aliphatic and cycloaliphatic aldehydes, aliphatic and cycloaliphatic ketones and, especially, esters of aliphatic and cycloaliphatic carboxylic acids with hydrogen in the presence of a catalytic amount of the catalyst composition described hereinabove. As used herein, the terms "carbonyl containing compounds" are intended to include compounds of the structure

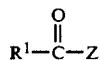

wherein

R$^1$ is a C$_1$–C$_{20}$ alkyl or substituted alkyl radical (including cycloalkyl radicals) or a C$_2$–C$_{20}$ alkenyl (including cycloalkenyl) or alkynyl (including cycloalkynyl) radical or substituted derivative thereof wherein said substituted groups include ethers, amines, additional carbonyl groups, aryl groups, hydroxyl groups and alkoxy groups; and Z is a hydrogen; R$^2$ wherein R$^2$ is selected from R$^1$, C$_6$–C$_{20}$ aryl or substituted aryl and is selected independently of R$^1$; and OR$^2$ wherein R$^2$ is as defined herein; provided that R$^1$ and Z can be joined as part of a polymethylene or hydrocarbyl or heteroatom-substituted polymethylene radical.

The esters which may be hydrogenated in accordance with the process provided by this invention are aliphatic, cycloaliphatic and aromatic esters of aliphatic and cycloaliphatic mono. and poly-carboxylic acids. The carboxylic acid residue of the ester reactants is not important to our process provided that each oxycarbonyl group hydrogenated is bonded to an aliphatic or cycloaliphatic carbon atom. For example, esters of arylcarboxylic acids such as alkyl benzoates are not included in the ester reactant in the process whereas esters of aralkylcarboxylic acids such as alkyl phenylacetates are included within the meaning of esters of aliphatic acids. The aliphatic acid residues may be straight- or branched-chain, saturated or unsaturated and unsubstituted or substituted, for example with a wide variety of substituents such as hydroxy, alkoxy, amino, substituted amino, acylamido, aryl, cycloalkyl, etc. The main chain of the aliphatic acid residues may contain hetero atoms such as oxygen, sulfur and nitrogen atoms.

Exemplary carbonyl-containing compounds conforming to the above formula include alkyl oleates, dialkyl adipates, propionaldehyde, dialkyl cyclohexane dicarboxylates, alkyl acrylates, alkyl propionates, alkyl isobutyrates, alkyl normal butyrates, alkyl acetates, nonanal, dialkyl butane dicarboxylates, alkyl methacrylates, alkyl crotonates, alkyl sorbates, alkyl cinnamates, maleic anhydride, alkyl fumarates, dialkyl succinates, succinic anhydride, alkyl glutarates, dialkyl malonates, dialkyl octanedioates, dialkyl decanedioates, dialkyl dodecanedioates, alkyl laurates, alkyl myristates, alkyl palmitates, alkyl stearates, alkyl linoleates, alkyl linolenates, alkyl isovalerates, alkyl normal valerates, alkyl caproates, alkyl caprylates, alkyl 2-ethylhexanoates, dialkyl acetates, alkyl cyclohexane carboxylates, alkyl pyruvates, alkyl glycolates, alkyl oxalates, alkyl formates, alkyl lactates, alkyl citrates, glyceride esters, and the like. Typical alkyl groups employed have from 1 up to 20 carbon atoms, with alkyl groups having 1 up to 6 carbon atoms being preferred.

Preferred carbonyl-containing compounds are compounds selected from the group consisting of:

wherein A is an alkylene moiety, an alkenylene moiety, or an alkynylene moiety having 1 up to 20 carbon atoms, or substituted derivative thereof, or a cycloalkylene or cycloalkenylene moiety having 4–12 carbon atoms or substituted derivative thereof; and wherein each Y is independently a C$_1$ up to C$_{12}$ alkyl, alkenyl or alkynyl radical or substituted derivative thereof;

wherein B is an alkyl, cycloalkyl, alkenyl, cycloalkenyl, alkynyl or cycloalkynyl radical, or substituted derivative thereof, having 1 up to 20 carbon atoms and Y is defined above;

wherein Q is an alkyl, cycloalkyl, alkenyl, cycloalkenyl, alkynyl or cycloalkynyl radical having 1 up to 20 carbon atoms or substituted derivatives thereof; and mixtures of any two or more thereof.

Typically, the ester reactants employed in our process may contain up to about 40 carbon atoms. Examples of the carboxylic acid esters include the aliphatic, cycloaliphatic and aromatic esters of acetic, propionic, butyric, valeric, hexanoic, heptanoic, octanoic, nonanoic, decanoic, undecanoic, lauric, tridecanoic, myristic, pentadecanoic, palmitic, heptadecanoic, stearic, oleic, linoleic, linolenic, nonadecanoic, eicosanoic, arachidonic, heneicosanoic, docosanoic, tetracosanoic, octacosanoic, triacontanoic, dotriacontanoic, acrylic, methacrylic, crotonic, 3-butenoic, cyclobutanecarboxylic, 2-norbornanecarboxylic, malonic, succinic, glutaric, maleic, glutaconic, adipic, pimelic, suberic, azelaic, sebacic, 1,2,4-hexanetricarboxylic, 1,2-, 1,3-, and 1,4-cyclohexanedi- carboxylic, 2,6 and 2,7-octahydro. naphthalenedicarboxylic, 3-[(2-carboxyethyl)thio]-butyric, etc. The alcohol segment of the ester reactants may be the residue of any mono- or poly-hydroxy compound such as methanol, ethanol, butanol, 2-butanol, 2-ethylhexanol, 2,2-dimethyl -1,3-propanediol, ethylene glycol, propylene glycol, 1,4-butanediol, 1,6-hexanediol, 1,10-decanediol, diethylene glycol, glycerin, trimethylolpropane, cyclohexanol, benzyl alcohol, phenol, hydroquinone, etc. The hydrogenation process provided by our invention is particularly useful for converting lower, i.e., $C_1-C_4$, alkyl esters, especially methyl esters, of $C_{10}-C_{20}$ carboxylic acids and cyclohexanedicarboxylic acids, e.g., dimethyl 1,3- and 1,4-cyclohexanedicarboxylic acid.

The hydrogenation process of the present invention involves contacting at least one of the above-described carbonyl-containing compounds with at least one of the above-described supported palladium/zinc catalysts in the presence of hydrogen under hydrogenation conditions. Hydrogenation conditions typically employed in the practice of the present invention are set forth below.

The process of the present invention can be operated in a variety of configurations. Depending on the substrate to be hydrogenated, the preferred method of operation is frequently in a fixed-bed flow reaction system. If the vapor pressure of the substrate to be hydrogenated is sufficiently high at reaction temperature, the desired method of operation may be vapor phase, i.e., all reactants and products exist in the gaseous phase. For other substrates, the desired method of operation may be a trickle bed configuration. Regardless of the method of operation, the desired time of contact between the reactants and catalyst components can be varied as desired to achieve the desired level of reaction.

In typical fixed bed operation, hydrogen pressures in the range of 100–10,000 psig may be employed. Preferably, the hydrogen pressure will be in the range of 500–3500 psig. Similarly, temperatures in the range of 25°–400° C. can be used, with a range of 100°–350° C., especially 150° to 350° C. in the hydrogenation of esters, being preferred. While the feed rate of the substrate will be varied to control the level of conversion, normal liquid hourly space velocities (LHSV) will be in the range of about 0.01–100 $h^{-1}$, with a preferred range of 0.1–20 $h^{-1}$. The molar ratio of hydrogen to substrate will typically be in the range of 1:1 to 1000:1 with a preferred range of 2:1 to 100:1.

Alternatively the invention may be conducted in a slurry phase reactor. In slurry phase operation, the ratio of carbonyl-containing compound to catalyst employed can vary widely, with ratios as low as 1:1 or lower being operable, but not economically attractive; and ratios as high as 10,000:1 and higher also being operable, but generally providing relatively low conversions unless very long contact times are employed. Preferred carbonyl-containing compound: catalyst ratios fall within the range of about 1:1 up to 1,000:1, with ratios in the range of about 2:1 up to 100:1 being most preferred because good levels of conversion of the carbonyl-containing compounds are obtained without requiring excessive amounts of catalyst, or extremely long contact times.

The hydrogenation process can be carried out in the absence or presence of a solvent, e.g., compounds which are fluid and in which the carbonyl-containing starting material is soluble at reaction temperature, and which are non-reactive under hydrogenation conditions. Preferred solvents are those which are fluid and in which the carbonyl-containing starting material is soluble at room temperature. Exemplary solvents include aromatic solvents such as toluene; alcohols such as methanol; ethers such as diphenyl ether and tetrahydrofuran; and the like. When employed, the volume/volume ratio of solvent to substrate can vary widely, typically falling in the range of about 5:95 to 95:5.

In accordance with another embodiment of the present invention, hydrogenation of carbonyl-containing compounds can be carried out with small amounts of water (i.e., 0.01 up to about 2 wt. % water based on the total weight of reactants and solvent) present in the reaction mixture. It has been found that selectivity to hydrogenation (as opposed to transesterification between reactant and product) products is greatly improved by the presence of such small quantities of water in the reaction mixture with similar catalysts.

Following hydrogenation, the desired product can be recovered and purified using conventional techniques well known to those of skill in the art. For example, catalyst can be removed from the reaction mixture by filtration, decantation and the like. By-products and unreacted starting material as well as solvent, if employed, can be separated from the product by distillation, recrystallization, solvent/solvent extraction, and the like.

The invention will now be described in greater detail by reference to the following non-limiting examples.

EXAMPLES 1 AND 2 AND COMPARATIVE EXAMPLES 1 AND 2

A sample of 2.8 weight percent palladium on silica (Davidson Grade 59 $SiO_2$) was prepared by dissolving 7 grams (g) of $[Pd(NH_3)_4]Cl_2$ in 25 mL of water and adding the resulting solution to about 100 g of the $SiO_2$ support material which was suspended in about 2,000 mL of water containing sufficient $NH_4OH$ to adjust the pH to about 11.0. After soaking for about two hours at room temperature, the silica was recovered by filtration, washed with about 400 mL of water, then dried in air at 120° C. for about 18 hours and then further treated to reducing conditions as follows:
 (a) 500 standard cubic centimeters per minute (sccm) of argon for about 1 hour at room temperature;
 (b) 500 sccm of argon for an additional 1 hour at 120° C.;
 (c) 500 sccm of argon for an additional 1 hour at 260° C.;
 (d) argon flow was replaced with hydrogen and catalyst temperature increased; hydrogen flow was maintained for about 1.5 hours after the temperature had reached about 400° C.; then
 (e) the catalyst was allowed to cool to about 380° C., the hydrogen flow replaced with about 500 sccm of argon, and catalyst then allowed to cool to room temperature under continued argon flow.

Zinc was added to 4–20 g portions of the palladium impregnated silica by dissolving the appropriate amount of zinc nitrate [Zn(NO$_3$)$_2$-6H$_2$O] in about 50 mL of water and adding this solution to the Pd/SiO$_2$ sample. The resulting solid was dried initially by stirring to steam bath temperature, followed by heating to about 120° C. in air and then calcined in flowing air at 200° C. for 3 hours prior to evaluation for hydrogenation of carbonyl-containing compounds. The weight percent palladium, based on the total weight of the palladium and the silica support, and the palladium:zinc atomic ratio (Pd:Zn) for each of the 4 catalysts prepared are shown in Table I.

COMPARATIVE EXAMPLE 3

The general procedure described above was repeated except that the palladium-impregnated silica was not treated as described but was only dried at 120° C. for 24 hours in air. After the addition of zinc as described above, the palladium- and zinc-impregnated silica was dried at 90° C. in air and then calcined at 200° C. for 3 hours. The weight percent palladium, based on the total weight of the palladium and the silica support, and the palladium:zinc atomic ratio (Pd:Zn) for the catalyst thus prepared are shown in Table I.

COMPARATIVE EXAMPLES 4 AND 5

The pH of a mixture of 3.08 g silica (Davidson Grade 59 SiO$_2$) in 245 mL deionized water was adjust to 11 by the addition of 12 mL ammonium hydroxide. The resulting mixture was stirred for 1.5 hours and then the silica was filtered, washed with 150 mL water and dried at 120° C. for 24 hours. A solution of 0.467 g of zinc nitrate in 6 mL water was stirred for 15 minutes with the ammonium hydroxide-treated silica. The zinc-bearing silica was calcined in air for 3 hours at 200° C. The resulting composition (Comparative Example 4) contained approximately 3 weight percent zinc calculated as the metal and based on the total weight of the zinc and silica.

The catalyst of Comparative Example 5 consisted of the palladium-impregnated silica prepared and treated as described in Example 1.

TABLE I

| Example | Weight Percent Palladium | Pd:Zn |
| --- | --- | --- |
| 1 | 2.8 | 1:1 |
| 2 | 2.8 | 1:2 |
| C-1 | 2.8 | 1:5 |
| C-2 | 2.8 | 1:10 |
| C-3 | 2.8 | 1:2 |
| C-4 | — | 0:1 |
| C-5 | 2.8 | 1:0 |

EXAMPLES 3 AND 4 AND COMPARATIVE EXAMPLES 6-10

The catalysts prepared in the preceding examples were evaluated in the vapor phase hydrogenation of methyl acetate using 1-2 cc of powdered catalyst. The apparatus used consisted of a 0.25 inch interior diameter, stainless steel, tubular reactor containing the catalyst which was held in place with quartz wool plugs above and below the catalyst bed. The central portion of the tube was encased in an electric furnace with a thermocouple fixed in the catalyst bed. Hydrogen and methyl acetate were fed, using a Brooks flow controller and an Eldex pump, to the top of the reactor in a hydrogen:methyl acetate mole ratio of 3.6:1 to 4.5:1. The evaluations were carried out at a temperature of 300° C. and a pressure of 750 psig using a gas hourly space velocity (GHSV), which is the mL of gas fed per hour divided by the mL of catalyst bed, of approximately 30,000 h$^{-1}$ at conversions of less than 20 percent. The pressure of the off-gas removed from the bottom of the reactor was reduced to atmospheric pressure, cooled in a glycol condenser system and the resulting liquid and gas phases were analyzed by gas chromatography. The results obtained are set forth in Table II wherein the conversion rates to methanol (MeOH), ethanol (EtOH) and ethyl acetate (EtOAc) are given in micromoles per g catalyst per second and "Total" is the sum of conversion to ethanol plus ethyl acetate. The numerical designation for the catalyst (Cat) used in each hydrogenation example refers to the catalyst set forth in Table I above.

TABLE II

| | | Rate of Conversion to | | | |
| --- | --- | --- | --- | --- | --- |
| Example | Catalyst | MeOH | EtOH | EtOAc | Total |
| 3 | 1 | 46.0 | 24.0 | 14.0 | 38.0 |
| 4 | 2 | 48.0 | 16.0 | 19.0 | 35.0 |
| C-6 | C-1 | 6.7 | 0.7 | 2.8 | 3.5 |
| C-7 | C-2 | 2.6 | 0.08 | 1.1 | 1.2 |
| C-8 | C-3 | 8.7 | 3.7 | 3.1 | 6.8 |
| C-9 | C-4 | 0.0 | 0.0 | 0.0 | 0.0 |
| C-10 | C-5 | 21.0 | 3.5 | 2.1 | 5.6 |

The results set forth in Table II demonstrate that catalysts comprising palladium and zinc on a silica support wherein the palladium:zinc ratio is 0.5 to 1 are superior to the corresponding supported monometallic samples and produce results superior to those obtained with palladium- and zinc-containing, supported catalysts which were not prepared in accordance with the present invention.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

I claim:

1. Process for hydrogenating an ester of an aliphatic or cycloaliphatic carboxylic acid to obtain the alcohol corresponding to the acid residue of the ester which comprises contacting the ester with hydrogen at a temperature of about 150° to 350° C. and a hydrogen pressure of about 500 to 3500 psig in the presence of a catalyst comprising palladium and zinc on a support wherein the palladium content of the catalyst is about 0.5 to 5.0 weight percent, calculated as the metal and based on the weight of the palladium, zinc and support, and the atomic ratio of palladium to zinc is about 0.2 to 2.0 and wherein the catalyst is obtained by the steps comprising:

(a) providing a catalyst support material on which is deposited zero-valent palladium in a uniformly and highly dispersed form;

(b) contacting the palladium-bearing support material of (a) with zinc or a reducible compound thereof; and (c) heating the palladium- and zinc-bearing support of (b) at a temperature of about 200° to 400° C. in the presence of an oxygen-containing gas.

2. Process according to claim 1 wherein the ester is dimethyl 1,4-cyclohexanedicarboxylate.

3. Process according to claim 1 wherein the ester is a lower alkyl ester of a $C_{10}$–$C_{20}$ carboxylic acid.

4. Process according to claim 1 wherein the ester is a di-lower alkyl adipate.

5. Process according to claim 1 wherein the ester is a di-lower alkyl maleate.

6. Process for hydrogenating methyl acetate to obtain ethanol which comprises contacting the methyl acetate with hydrogen at a temperature of about 150° to 350° C. and a hydrogen pressure of about 500 to 3500 psig in the presence of a catalyst comprising palladium and zinc on a support wherein the palladium content of the catalyst is about 0.5 to 5.0 weight percent, calculated as the metal and based on the weight of the palladium, zinc and support, and the atomic ratio of palladium to zinc is about 0.2 to 2.0 and wherein the catalyst is obtained by the steps comprising:

(a) providing a catalyst support material on which is deposited zero-valent palladium in a uniformly and highly dispersed form;

(b) contacting the palladium-bearing support material of (a) with zinc or a reducible compound thereof; and (c) heating the palladium- and zinc-bearing support of (b) at a temperature of about 200° to 400° C. int he presence of an oxygen-containing gas.

* * * * *